United States Patent
Dutta et al.

(10) Patent No.: US 10,187,953 B1
(45) Date of Patent: Jan. 22, 2019

(54) LAMP PROJECTING LIGHT WAVELENGTHS FOR GENERAL ILLUMINATION AND ILLUMINATION THAT DOES NOT ATTRACT INSECTS

(71) Applicants: Arunava Dutta, Winchester, MA (US); Anne Janet Milliez, Cambridge, MA (US); Ming Li, Acton, MA (US)

(72) Inventors: Arunava Dutta, Winchester, MA (US); Anne Janet Milliez, Cambridge, MA (US); Ming Li, Acton, MA (US)

( * ) Notice: Subject to any disclaimer, the term of this patent is extended or adjusted under 35 U.S.C. 154(b) by 0 days.

(21) Appl. No.: 15/833,318

(22) Filed: Dec. 6, 2017

(51) Int. Cl.
*F21V 9/00* (2018.01)
*H05B 33/08* (2006.01)
*F21K 9/232* (2016.01)

(52) U.S. Cl.
CPC ......... *H05B 33/0863* (2013.01); *F21K 9/232* (2016.08); *H05B 33/0896* (2013.01)

(58) Field of Classification Search
CPC ............................ H01L 25/07; H05B 33/0863
USPC ........................ 313/498; 362/180, 231, 185
See application file for complete search history.

(56) References Cited

U.S. PATENT DOCUMENTS

| | | | |
|---|---|---|---|
| 7,387,402 B1* | 6/2008 | Lui (Phillip) | F21L 4/027 362/180 |
| 2008/0030138 A1* | 2/2008 | Turner | F21V 9/08 313/634 |
| 2013/0169146 A1* | 7/2013 | Aoki | H01L 33/44 313/498 |
| 2013/0241391 A1* | 9/2013 | Takei | H01L 25/0753 313/498 |

* cited by examiner

*Primary Examiner* — Daniel A Hess (57) ABSTRACT

A lamp including a first group of solid state light emitters that produce a general illumination light mode. The general illumination light mode is provided by a first range of light wavelengths emitted by the first group of solid state light emitters having a correlated color temperature ranging from 2700K to 6500K. The lamp also includes a second group of solid state light emitters that emit a second range of light wavelengths that are not visible to insects in a substantially insect free illumination light mode. The second range of light wavelengths have a spectral power ratio of wavelengths of less than substantially 550 nm to a total spectra of less than 700 nm, that is equal to 5.8% or less. The lamp further includes the ability to switch between the two modes of light.

17 Claims, 6 Drawing Sheets

LAMP PROJECTING LIGHT WAVELENGTHS FOR GENERAL ILLUMINATION AND ILLUMINATION THAT DOES NOT ATTRACT INSECTS

TECHNICAL FIELD

The present disclosure generally relates to lighting, and more particularly to lamps that project light wavelengths that do not attract insects.

BACKGROUND

Bug lamps, which may be described as lamps that project light wavelengths that do not attract insects, have conventionally been provided by incandescent lamps with a coating applied on the interior of the bulb to emit wavelengths of light for light that appears yellowish in color. The reason for the yellowish color was that common bugs are less attracted to this general color of light so when this bug lamp was switched on in the home porch, one could enjoy the outdoors without being bothered by insects that would normally be attracted to a general illumination lamp.

SUMMARY

In one aspect, a lamp is provided having light sources for producing at least two spectra of light waves. Each of the at least two spectra of light waves correspond to a mode of lighting. For example, there is an insect free illumination light mode that includes wavelengths outside the wavelengths of light that are visible to insects. Additionally, the same lamp assembly includes a general illumination light mode, which can provide additional wavelengths the provide for additionally wavelengths that can provide brighter lighting, e.g., greater luminous flux, and/or different colors. The wavelengths of the general illumination light mode may include light that is more generally pleasing to humans wanting illumination in dark settings without eliminating wavelengths that could attract insects.

The lamp further includes the ability to switch between the two modes of light. In accordance with this aspect of the lamp, a user may be able to use the general illumination light mode to light a room for any purpose, e.g., to provide an optimum brightness for people to relax on the porch of a home at night, providing the optimized light for that purpose; and in the event that insects are within the area and attracted to the light emitted by the general illumination light mode, the user may easily switch the lighting mode of the lamp to the insect free illumination light mode that includes wavelengths outside the wavelengths that are visible to insects. In some embodiments, by switching the lighting mode to the insect free illumination mode, which includes primarily wavelengths of light that are outside the wavelengths of light that are visible to insects, the insects will no longer be attracted to the lamp, and will leave the area in which the lamp is present. The term "primarily" denotes that the insect free illumination light mode may have some wavelengths below 550 nm, but the power in that region of wavelengths, i.e., below 550 nm, is the vast minority of power of wavelengths for the light emitted by the insect free illumination light mode, as illustrated by the insect visible ratio for the light emitted during the insect free illumination light mode, which is further characterized below.

In one embodiment, the lamp, i.e., lamp assembly, includes a housing including a body for containing light sources. The body has a first end for engagement to an electrical source for energizing the light sources contained within the body for illumination. The body also includes a second end having a lens through which the light sources emit light. The lamp further includes a first group of solid state light emitters providing one grouping of said light sources contained within the housing. Illuminating the first group of solid state light emitters produces a general illumination light mode. The general illumination light mode is provided by a first range of light wavelengths emitted by the first group of solid state light emitters. The lamp further includes a second group of solid state light emitters providing another grouping of the light sources contained within the housing. Illuminating the second group of the light sources contained within the housing produces a substantially insect free illumination light mode that emits a second range of light wavelengths that are not visible to insects. The second range of wavelengths having a substantial majority being greater than 550 nm. In some embodiments, the lamp further includes a driver that is responsive to a switch to illuminate only one of the two groups of light sources at a time so that the two groups of light sources can not emit light simultaneously.

In another embodiment, the lamp may include a housing including a body for containing light sources, in which the body has a first end for engagement to an electrical source for energizing the light sources contained within the body, and the body includes a second end having a lens through which the light sources emit light. In some embodiments, the lamp includes a first group of solid state light emitters providing one grouping of said light sources contained within the housing. When illuminated, the first group of solid state light emitters produces a general illumination light mode that is provided by a first range of light wavelengths having a correlated color temperature ranging from 2700K to 6500K. In some embodiments, the lamp includes a second group of solid state light emitters providing another grouping of said light sources contained within the housing. When illuminated, the second group of said light sources contained within the housing emits a second range of light wavelengths that are substantially not visible to insects. The second range of light wavelengths can have a spectral power ratio of wavelengths for wavelengths of less than substantially 550 nm (between 400 nm and 550 nm) to a total spectra of less than 700 nm (between 400 nm and 700 nm) that is equal to 5.8% or less.

In another aspect of the present disclosure, a method of illumination is provided, in which the lamp includes at least two light sources producing at least two spectra of light waves. Each of the at least two spectra of light waves correspond to a mode of lighting. For example, there is an insect free illumination light mode that includes wavelengths substantially outside the wavelengths that are visible to insects. Additionally, the same lamp assembly includes a general illumination light mode, which can provide additional wavelengths that can provide brighter lighting, e.g., greater luminous flux, and/or different colors.

In one embodiment, the method includes energizing one grouping of solid state light sources in a lamp having a plurality of solid state light sources enclosed behind a single lens within a single lamp housing. The selected grouping of solid state light sources being energized by a driver that is responsive to an external switch. The method may further include switching from a first grouping of solid state light sources for a general lighting mode of the lamp that emits first light wavelengths that include light that is visible to insects to a second grouping of solid state light sources emitting second light wavelengths that in their majority are not visible to insects, the second range of light wavelengths having a spectral power ratio for wavelengths of less than substantially 550 nm (between 400 nm and 550 nm) to a total spectra of less than 700 nm (between 400 nm and 700 nm) that is equal to 5.8% or less.

BRIEF DESCRIPTION OF THE DRAWINGS

The following description will provide details of embodiments with reference to the following figures wherein.

DETAILED DESCRIPTION

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

Bug lamps include lamps that emit spectra of light that do not substantially attract insects, such as flies, mosquitoes, gnats, stable flies, horse flies, face flies, deer flies, horn flies, fleas, wasps, flying moths, cockroaches, crickets, ants, spiders, carpet beetles, centipedes, silverfish, bed bugs and combinations thereof, have conventionally been provided by incandescent lamps. In some instances, the wavelengths of light that do not attract insects have a yellow appearance in color, and it has been determined that the level of luminous flux produced by incandescent type bug lights is far lower than would be required for general illumination. For example, the luminous flux for an incandescent bug lamp may range from 100 lm to 450 lm. Luminous flux is the measure of the perceived power of light, which may be characterized in units of lumen (lm).

In view of this deficiency, the bug lamp is generally not suitable for general illumination in the hours before dusk falls. In addition to the lumen deficiency, the yellowish color of light produced by the bug lamp is also not ideal for general illumination. Bug lamps in some examples have transitioned in technology from incandescent based lighting to LED based lighting. This can make the lamp much more efficient in terms of electrical power consumption. For example an incandescent bug lamp may have consumed 40 W to 60 W whereas today's LED based bug lamps could use only about 5 W to 8 W for example. No LED based lighting systems prior to the methods and structures described herein can provide for both general illumination, and as having a light that specifically does not attract insects, which is emitted from the same lamp. In some embodiments, the methods and structures described herein provide a lamp which provides both as a general illumination lamp and as a bug lamp from the same light source.

For example, the lamp may have multiple modes of illumination, such as a general illumination light mode and a substantially insect free illumination light mode, in which the wavelengths of light emitted by the light source of the lamp during the substantially insect free illumination light mode have substantially minimized light wavelengths that are visible to insects. This can provide that a home owner will only need just one lamp that would be able to perform both functions, i.e., the functions of general illumination and substantially free insect illumination, on demand. In some embodiments, an operator can be easily able to invoke either mode of lamp operation, general illumination of the porch or bug lamp operation, without having to resort to a smart phone and/or using smart phone or computer based applications, i.e., apps. In some instances, the lamp structure described in the present disclosure may be referred to as a "two-in-one bug lamp". The term "two in one" referring to the light spectrum being emitted by the lamp of at least two range of spectra that include a first spectra of light having the characteristics for "general illumination lighting", and a second spectra of light having the characteristics for "substantially insect free illumination lighting". The term "substantially insect free illumination lighting" denotes that the majority of wavelengths of light is more than 550 nm, which is not visible to insects. It has been determined that in general wavelengths of light above 550 nm are not visible to many insects. The lighting spectra for "general illumination lighting" may range from 400 nm to 700 nm, which is the entire visible range of human beings. In some embodiments, the two-in-one lamp described herein is superior in bug function, i.e., providing substantially insect free lighting, to the other bug lamps in the market terms in terms of its distinctly lower insect visible ratio. The insect visible ratio is defined as the spectral power <550 nm (which is substantially visible to most insects) as a ratio of the spectral power in the whole visible spectrum (400 nm-700 nm) that is detectable and observable to the human eye. As will be described in greater detail below, the insect visible ratio of light emitted by the lamp structures described in accordance with the methods and structures of some embodiments of the present invention is equal to 5.8% or less. Various embodiments of the spectrum of the disclosed lamp are presented. The methods, structures and assemblies of the present disclosure are now described with further detail with reference to FIGS. 1-10.

Figure 1:
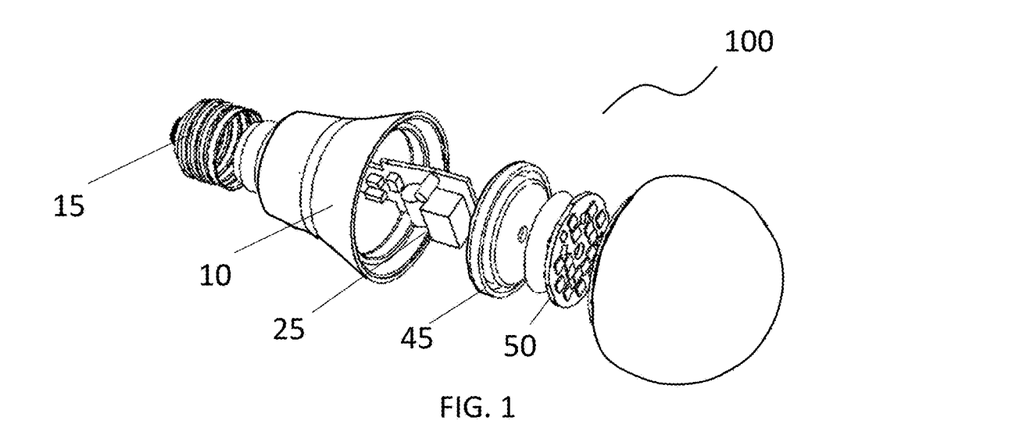
FIG. 1 is an exploded perspective view of a lamp including a light source provided by a light engine configuration that includes at least two groupings of solid state light emitters, i.e., a first string of light emitting diodes that emit light having wavelengths for a general illumination light mode of lighting, and a second string of light emitting diodes that emit light having wavelengths for a substantially insect free illumination light mode, in accordance with one embodiment of the present disclosure.
Figure 2:
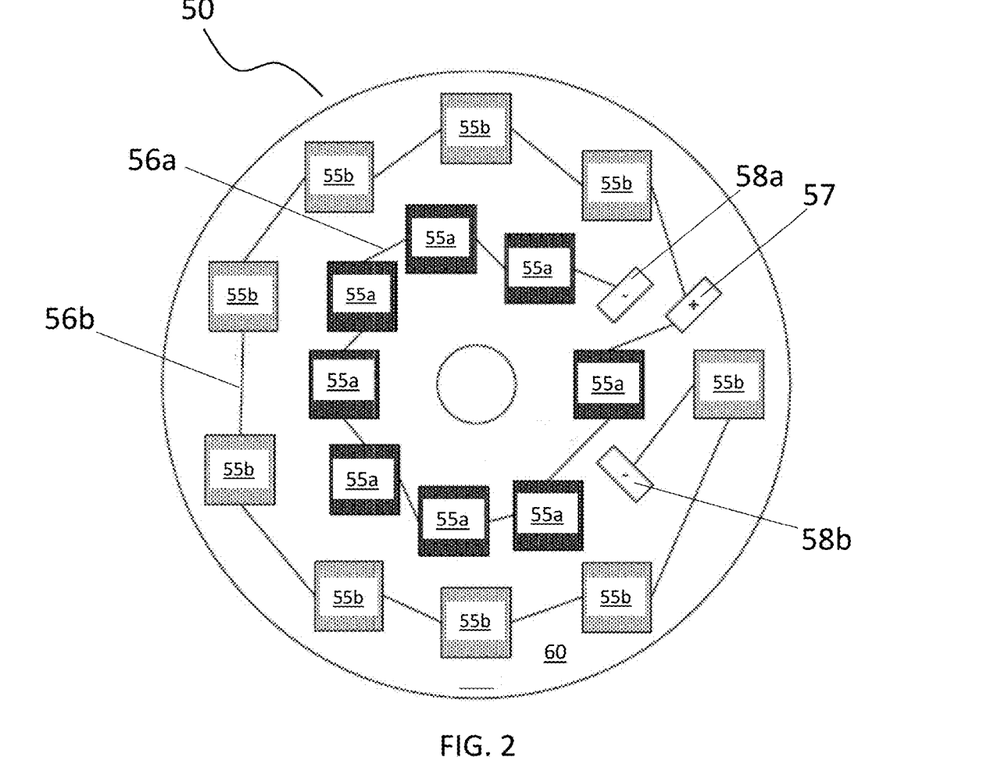
FIG. 2 is a top down view of a light engine configuration including a plurality of solid state light emitter providing the light source of a lamp that provides at least two modes of lighting including an insect free illumination light mode, in accordance with one embodiment of the present disclosure.
Figure 3:
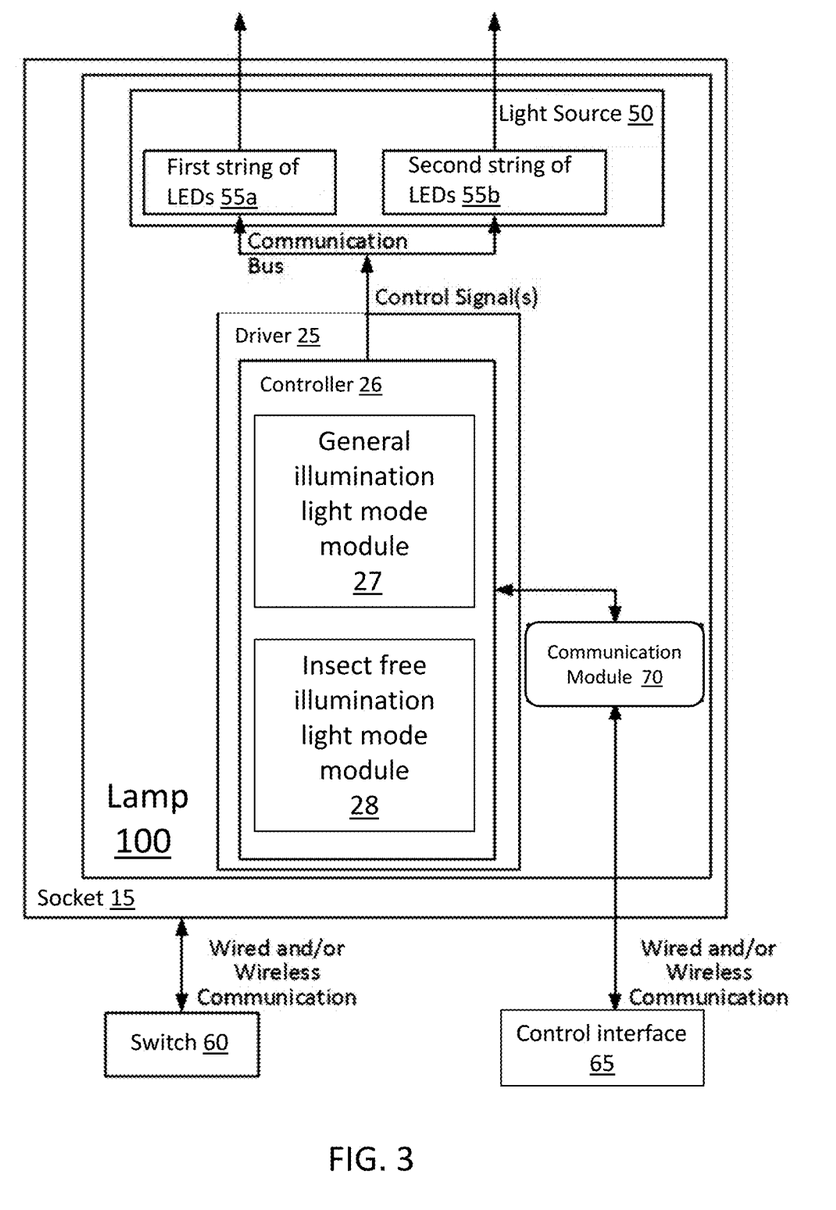
FIG. 3 is a block diagram illustrating the integration of light engine configuration and the lamp depicted in FIGS. 1 and 2 with a driver and switch to a power source, in accordance with one embodiment of the present disclosure.

Referring to FIGS. 1-3, the lamp 100 employs solid state light emitters, e.g., light emitting diodes (LEDs), to provide the general light illumination light mode and the insect free light illumination light mode. The term "solid state" refers to light emitted by solid-state electroluminescence, as opposed to incandescent bulbs (which use thermal radiation) or fluorescent tubes, which use a low pressure Hg discharge. Compared to incandescent lighting, solid state lighting creates visible light with reduced heat generation and less energy dissipation. Some examples of solid state light emitters that are suitable for the methods and structures described herein include inorganic semiconductor light-emitting diodes (LEDs), organic light-emitting diodes (OLED), polymer light-emitting diodes (PLED) or combinations thereof. Although the following description describes an embodiment in which the solid state light emitters are provided by light emitting diodes, any of the aforementioned solid state light emitters may be substituted for the LEDs.

Referring to FIG. 1, in one embodiment, the lamp 100 includes a housing including a body 10 for containing a light source 50 (or multiple light sources). The body 10 having a first end, e.g., lamp base 15, for engagement to an electrical source for energizing the light sources 50 contained within the body 10, and the body 10 includes a second end having an optic 20, e.g., lens, through which the light sources 50 emit light. Referring to FIGS. 1 and 2, the lamp 100 also includes a first group of solid state light emitters, e.g., first string of LEDs 55a, providing one grouping of the light sources 50 contained within the body 10 of the housing, wherein illuminated the first group of solid state light emitters produces a general illumination light mode provided by a first range of light wavelengths emitted by the first group of solid state light emitters, e.g., LEDs. Referring to FIGS. 1 and 2, a second group of solid state light emitters, e.g., second string of LEDs 55b, provides another grouping for the light sources contained within the housing, wherein when illuminated the second group of the light sources 55b contained within the housing produces a substantially insect free illumination light mode that emits a second range of light wavelengths that are not visible to insects. The second range of wavelengths can have a substantial majority being greater than 550 nm. The second range of light wavelengths having a spectral power ratio of wavelengths of less than substantially 550 nm to a total spectra of less than 700 nm, i.e., an insect visible ratio, that is equal to 5.8% or less. Referring to FIG. 1, the lamp 100 further includes a driver 25 to illuminate only one of the two groups of light sources, i.e., only one of the strings of LEDs 55a, 55b, at a time so that the two groups of light sources can not emit light simultaneously.

Referring to FIG. 2, in some embodiments, the light source 50 (also referred to as light engine) for the lamp 100 is provided by at least two strings of LEDs 55a, 55b, i.e., a first string 55a provides the general illumination and a second string 55b provides the bug lamp spectrum, i.e., the substantially insect free illumination light mode of the lamp 100. The LEDs that provide the two strings of LEDs 55a, 55b can be mounted to the circuit board 60 by solder, a snap-fit connection, or other engagement mechanisms. In some examples, the LEDs are provided by a plurality of surface mount device (SMD) light emitting diodes (LED).

The circuit board 60 for the light source 50 may be composed of a metal core printed circuit board (MCPB). MCPCB uses a thermally conductive dielectric layer to bond circuit layer with base metal (Aluminum or Copper). In some embodiments, the MCPCB use either Al or Cu or a mixture of special alloys as the base material to conduct heat away efficiently from the LEDs thereby keeping them cool to maintain high efficacy.

As depicted in FIG. 2, the light source 50 may include two strings of LEDs 55a, 55b that are mounted on a single circuit board 60 that provides a single substrate containing both the first string of LEDs 55a that emits light for the general illumination light mode, and the second string of LEDs 55b that emits light for the substantially insect free illumination light mode. When referring to a "string" of LEDs it is meant that each of the LEDs in the string are illuminated at the same time in response to an energizing act, such as the application of electricity from the driving electronics, e.g., driver 25, in the lamp 100. The LEDs in a string of LEDs are electrically connected for this purpose. For example, when the first string of LEDs 55a is energized for illumination, all of the LEDs in the string are illuminated. Further, in some embodiments, illuminating the first string of LEDs 55a does not illuminate the LEDs in the second string of LEDs 55b, and vice versa, as they are independently energized by the driving electronics, and not electrically connected. As depicted in FIG. 2, each of the LED strings 55a, 55b are connected by an electrical pathway 56a, 56b, which may be a wire, but is not necessarily a wire. Although there is a single positive contact 57 provided to both electrical pathways 56a, 56b to the first and second strings of LEDs 55a, 55b, there is a separate negative contact 58a, 58b for each of the electrical pathways 56a, 56b to the first and second string of LEDs 55a, 55b. This arrangements allows for separate energizing of the strings to allow for illumination of only one grouping of LEDs that is provided by only one string, in which selection of the string of LEDs for illumination can be provided by a controller 26 in the driver electronics 25. It is noted that the use of strings described above is only one example of how groups of LEDs, i.e., solid state light emitters, can be grouped to illuminate simultaneously. It is not necessary that this example be employed, so long as groupings of LEDs are provided, in which one grouping provides light having wavelengths of light that provide a substantially insect free lighting mode of illumination that in some embodiments is characterized by an insect visible ratio of light ((spectral power in total light wavelengths emitted less than 550 nm)/(spectral power in total light wavelengths emitted less than 700 nm) that is equal to 5.8% or less.

Additionally, although the present description refers to only two strings of LEDs 55a, 55b in describing some embodiments of the lamp 100, the lamp 100 is not limited to only two strings of LEDs 55a, 55b, so long as one of the groupings of LEDs 55a, 55b emits wavelengths of light that provide a substantially insect free lighting mode of illumination that in some embodiments is characterized by an insect visible ratio of light ((spectral power in total light wavelengths emitted less than 550 nm)/(spectral power in total light emitted less than 700 nm) that is equal to 5.8% or less. For example, the number of strings of LEDs, i.e., number of strings of solid state light emitters, may be equal to 2, 3, 4, 5, 6, 7, 8, 9, 10 and 15, as well as any range for the number of strings of LEDs having a lower endpoint to the range that is provided by one of the aforementioned examples, and having an upper endpoint to the range that is provided by one of the aforementioned examples.

The arrangement of LEDs, or other solid state light emitters of the light source 50, over the circuit board 60 may be customized, as desired for a given target application or end-use. In the embodiment that is depicted in FIG. 2, the LEDs interconnected to provide first and second strings of LEDs 55a, 55b may be arranged, e.g., concentrically, about the center region of circuit board 60, and LEDs, i.e., solid state light emitters, may be arranged, e.g., concentrically, about the perimeter region of circuit board 60. The quantity, density, and spacing between neighboring LEDs that provide the first and second string 55a, 55b on the circuit board 60 may be customized, as desired for a given target application or end-use. For example, a grid distribution may also be employed for arranging the LEDs, i.e., solid state light emitters, of the light source 50. Although in some instances the LEDs, i.e., solid state light emitters, may be equally spaced from one another, this is not necessary, as embodiments have been contemplated in which higher density regions of LEDs, i.e., solid state light emitters, are present on a specific portion of a circuit board 60 in comparison to the remainder of the circuit board 60.

In some embodiments, the LEDs in first string 55a are all of substantially the same color and can be of any desired correlated color temperature (CCT) between 3000 and 5000K, depending on the color of the white light that is preferred for the general illumination mode of light emitted from the lamp 100. The LEDs in the first string 55a are capable of emitting light wavelengths ranging from 400 nm to 700 nm. The wavelengths of light emitted by the first string of LEDs 55a may be referred to as the first range of wavelengths emitted by the lamp 100. These wavelengths are for the general illumination lighting mode. The wavelengths of light for the first range of wavelengths emitted by the first string of LEDs 55a is different than the wavelengths of light for second range of wavelengths emitted by the second string of LEDs 55b. The wavelengths of light for the first range of wavelengths emitted by the first string of LEDs 55a may include light wavelengths that are visible to insects, e.g., being less than 550 nm which would attract insects. Further, the wavelengths of light for the first range of wavelengths emitted by the first string of LEDs 55a may have a high insect visible ratio of light. For example, the insect visible ratio of light ((spectral power in total light wavelengths emitted less than 550 nm)/(total light emitted less than 700 nm)) for the wavelengths of light being emitted by the first string of LEDs 55a can be any value greater than 6%. The wavelengths of light selected for emission by the first string of LEDs 55a can be any type of light, which may be optimal for general illumination. For example, the wavelengths, as well as other characteristics of light, selected for general illumination lighting mode may be selected to provide the optimal lighting for outdoor porch illumination after dusk. Optimization of the light wavelengths for general illumination can include light wavelengths that would attract insects, because in the presence of insects, the user of the lamp 100 has the capability to turn the first string of LEDs 55a off, and instead provide for lighting with wavelengths that do not attract insects through the same lamp 100 by illuminating the second string of LEDs 55b.

In some embodiments, the LEDs in the first string 55a may be modified depending on the color of the white light that is preferred for the application of the illumination desired for the general illumination light mode, e.g., the preferred lighting for the illumination of a porch type setting during night hours. For example, other LEDS may be employed for the first string of LEDs 55a for emitting white light for the general illumination light mode with a correlated color temperature (CCT) between 2700K and 6500K, and any suitable color rendering index (CRI) between 70 and 95. In one example, the first string of LEDs 55a may include 8 Osram Duris S5 GW PSLR31.EM 4000K 80 CRI LEDs available from Osram Sylvania. It is noted that this is only example of a type of LEDs that may be employed in the first string of LEDs 55a that provides the general illumination light mode of the lamp. The present disclosure is not limited to only the aforementioned example of LEDs for the types of LEDs employed within the first string of LEDs 55a. For example, any white light emitting LED with a typical emission spectrum, similar to that depicted in FIG. 5, may be employed within the first string of LEDs 55a. Further, any type of white LED of any size similar to 2835 or 3030 can be used as an LED in the first string of LEDs 55a, as long as the LED meets the CCT, CRI and lumen needs of the lamp in the General Illumination mode.

It is further noted that although the specific example depicted in FIG. 2 illustrates a first string of LEDs 55a that includes eight (8) LEDs in the string, the first string of LEDs 55a is not limited to only this number of LEDs in the string. In some examples, the number of LEDs in the first string of LEDs 55a may be equal to 4, 5, 6, 7, 8, 9, 10, 11, 12, 13, 14, 15, or 20, as well as any range for the number of LEDs in the first string including one of the aforementioned examples as a lower endpoint of the range, and one of the aforementioned examples as an upper endpoint of the range. It is also noted, that in the embodiment depicted in FIG. 2, the LEDs in the first string of LEDs 55a may each be the same type of LED, i.e., each of the LEDs may emit light having the same characteristics, such as wavelength, color, correlated color temperature (CCT), intensity, as well as other similar type solid state light emitting device performance.

Still referring to FIG. 2, a second string of LEDs 55b that provides another grouping of LEDs for the light source 50 that is separate from the first string of LEDs 55a. In some embodiments, the second string of LEDs 55b emits a second range of light wavelengths that is different from the first range of light wavelengths that is emitted by the first string of LEDs 55a. The wavelengths of light emitted by the second string of LEDs 55b are selected to not be visible to insects, which means the wavelengths of light emitted by the second string of LEDs 55b does not attract insects, hence providing a substantially insect free illumination light mode. It has been determined that insects can view light having wavelengths of less than 550 nm. For example, insects are capable of detecting ultraviolet wavelength and some light color wavelengths using photoreceptors. For example, flies have UV receptors that are capable of detecting light waves having a peak ranging from 340 nm to 360 nm, while beetles are attracted to longer wavelengths having peaks ranging from 365 nm to 528 nm. The second string of LEDs can be designed to include wavelengths that specifically exclude wavelengths of light that attract insects, such as the aforementioned insects and wavelengths of light to which they are attracted. In some embodiments, by providing light wavelengths greater than 550 nm, the second string of LEDs 55b can illuminate an area without attracting insects.

It has also been determined that not only peak wavelengths need to be minimized, but light source, e.g., LEDs or other solid state light emitters, must be selected to minimize the incidence of any light wavelengths with the visible range of light wavelengths of insects, which is generally below 550 nm. This is referred to as the insect visible range. The "insect visible ratio" is the ratio of (spectral power in total light wavelengths emitted less than 550 nm)/(spectral power in total light wavelengths emitted less than 700 nm). It is the ratio of spectral power in the total wavelengths emitted by the LEDs, i.e., solid state light emitters, of the second string of LEDs 55b that are visible to insects, and therefore below 550 nm, to the spectral power in the wavelengths of light visible to humans, which is wavelengths less than 700 nm. In some embodiments, the second string of LEDs 55b of the light source 50 that provides the substantially insect free illumination light mode includes LEDs, which may include a combination of LEDs having different wavelengths, that provides an insect visible ratio that is equal to 5.8% or less. In this example, the second range of light wavelengths emitted by the second string of LEDs 55b has a spectral power ratio of wavelengths for wavelengths of less than substantially 550 nm to a total spectra less than 700 nm that is equal to 5.8% or less. In another embodiment, the second range of light wavelengths have a spectral power ratio of wavelengths of less than substantially 550 nm to a total spectra of less than 700 nm, i.e., the insect visible ratio, that is equal to 4.5% or less. In yet another embodiment, the second range of light wavelengths emitted by the second string of LEDs 55b have a spectral power ratio of wavelengths of less than substantially 550 nm to a total spectra of less than 700 nm, i.e, the insect visible ratio, that is equal to 1.5% or less. The aforementioned ranges for the insect visible ratio are illustrative and not intended to limit disclosure. Examples of insect visible ratios that are suitable for characterizing the light emitted by the second string of LEDs 55b for providing the substantially insect free illumination light mode include 0.05%, 0.25%, 0.5%, 0.75%, 1.0%, 1.25%, 1.5%, 1.75%, 2.0%, 2.25%, 2.5%, 2.75%, 3.0%, 3.25, 3.5%, 3.75%, 4.0%, 4.25%, 4.5%, 4.75%, 5.0%, 5.25%, 5.5%, 5.75% and 5.8%, as well as any range of insect visible ratio using one of the aforementioned examples as a lower limit of the range, and one of the aforementioned examples as an upper limit of the range. For example, the range of insect visible ratio that is used in some embodiments of the LEDs for the second string of LEDs 55b may range from 0.05% to 5.8%.

To provide the aforementioned wavelengths of light that are substantially not visible to insects, e.g., being greater than 550 nm, and to provide the aforementioned insect visible ratio of 5.8% or less, the second string of LEDs 55b may include three types of LEDs each having different spectral power distributions (SPD). The SPD of a LED quantifies how much spectral power there is at each of the wavelengths of light that the LED emits. For example, two types of LEDs may be employed for the second string of LEDs 55b including 6 Osram Duris S5 Amber GA PSLR31 LEDs and 3 Nichia NFSY757G LEDs in series. The spectral power distributions (SPD) for the Osram Duris S5 Amber GA PSLR31 LED is similar to the SPD depicted in FIG. 8. The spectral power distributions (SPD) for the Nichia NFSY757G LED is similar to the SPD depicted in FIG. 7. It can be seen that these two LEDs, i.e., the Osram Duris S5 Amber GA PSLR31 LED and the Nichia NFSY757G LED, have different shapes of the SPD. They also peak at different wavelengths with the Nichia type LEDs having a lower peak wavelength than the Osram LED. In addition, the full width half maximum (FWHM) is different for the two LEDs. The FWHM is the spread in wavelength between the two wavelengths at which the spectral power of the LED is 50% of the peak power. In some embodiments, any LED having an SPD similar to that depicted in FIG. 7 may be substituted for the Nichia NFSY757G LED in the second string of LEDs 55b. In some embodiments, any LED having an SPD similar to that depicted in FIG. 8 may be substituted for the Osram Duris S5 Amber GA PSLR31 LED in the second string of LEDs 55b. A grouping of LEDs of this type in a second string of LEDs 55b can provide an insect visible ratio for a substantially insect free illumination light mode that ranges from 4% to 4.5%.

Figure 6:
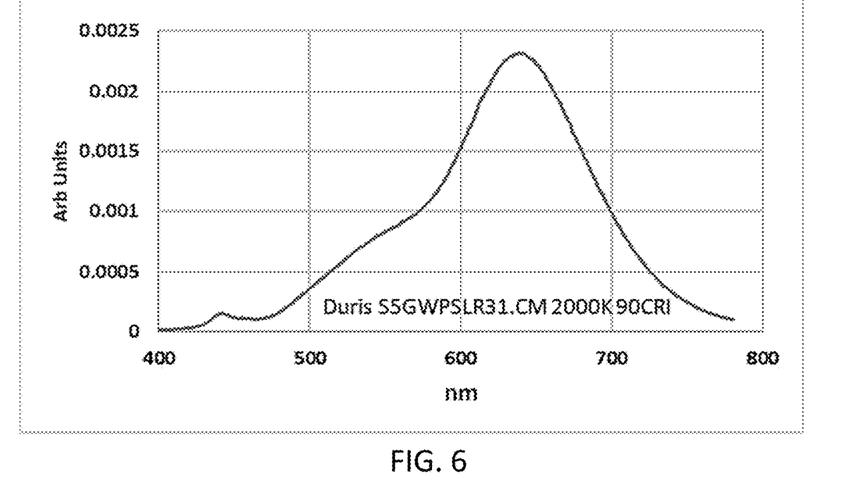
FIGS. 6-8 are each plots depicting a single spectral power distribution (SPD) of light emitted from a light emitting diode (LED) used in a second string of LEDs that provide a substantially insect free light mode in the light source of a test lamp sample including two modes of illumination, i.e., a general illumination light mode and an insect free illumination light mode.

In another example, two types of LEDs may be employed for the second string of LEDs 55b including 6 Osram Duris S5 Amber GA PSLR31 LEDs and 3 Osram Duris S5 GW PSLR31.CM 2000K 90 CRI LEDs. The spectral power distributions (SPD) for the Osram Duris S5 Amber GA PSLR31 LED is similar to the SPD depicted in FIG. 8. In some embodiments, any LED having an SPD similar to that depicted in FIG. 8 may be substituted for the Osram Duris S5 Amber GA PSLR31 LED in the second string of LEDs 55b. The spectral power distributions (SPD) for the Osram Duris 2000K LED is shown in FIG. 6. In some embodiments, any LED having an SPD similar to that depicted in FIG. 6 may be substituted for the Osram Duris 2000K LED in the second string of LEDs 55b. A grouping of LEDs of this type in a second string of LEDs 55b can provide an insect visible ratio for a substantially insect free illumination light mode that ranges from 5.5% to 5.8%.

In yet another example, the LEDs employed for the second string of LEDs 55b may include 9 Osram Duris S5 Amber GA PSLR31 LEDs. The spectral power distributions (SPD) for the Osram Duris S5 Amber GA PSLR31 LED is similar to the SPD depicted in FIG. 8. In some embodiments, any LED having an SPD similar to that depicted in FIG. 8 may be substituted for the Osram Duris S5 Amber GA PSLR31 LED in the second string of LEDs 55b. A grouping of LEDs of this type in a second string of LEDs 55b can provide an insect visible ratio for a substantially insect free illumination light mode that ranges from 1.25% to 1.75%. It is noted that the above examples are provided for illustrative purposes, and is not intended to be limiting. The lamp structures described herein may employ other LEDs with intrinsic SPD or emission spectra similar to those described above for the second string of LEDs 55b.

It is also noted that although the specific example depicted in FIG. 2 illustrates a second string of LEDs 55b that includes nine (9) LEDs in the string, the second string of LEDs 55b is not limited to only this number of LEDs in the string. In some examples, the number of LEDs in the second string of LEDs 55b may be equal to 4, 5, 6, 7, 8, 9, 10, 11, 12, 13, 14, 15, or 20, as well as any range for the number of LEDs in the second string including one of the aforementioned examples as a lower endpoint of the range, and one of the aforementioned examples as an upper endpoint of the range.

In addition to the LEDs, i.e., solid state light emitters, being selected to provide wavelength greater than 550 nm, and an insect visible ratio less than 5.8, the LEDs in the second string of LEDs 55b may have a color rending index (CRI) ranging from 70 to 95. Further, the light wavelengths emitted by the second string of LEDs 55b have a distribution with peak wavelength between 620 nm to 630 nm. In some embodiments, the light wavelengths emitted by the second string of LEDs 55b emit light wavelengths having a full width half maximum between 70 nm and 85 nm. Further, the light wavelengths emitted by the second string of LEDs 55b have a correlated color temperature (CCT) ranging from 1000 K to 1400 K.

The electrical power (wattage) of a given LED, i.e., solid state light emitter, in the first and second LED strings 55a, 55b may be customized, as desired for a given target application or end-use. In some embodiments, the LEDs may be low power (e.g. less than 0.25 W like the Nichia LEDs used in the bug light illumination mode) or they may be high power in which each LED has a wattage of about 1 W or less (e.g., the LEDs used in the general illumination mode or the other LEDs used in the bug light illumination mode, which are the S5 Amber and the Osram 2000K LEDs). In some cases, the LEDs may each be a high-power semiconductor light source having a wattage of about 1 W or greater (e.g., about 1.25 W or greater, about 1.5 W or greater, or any other sub-range in the range of about 1 W or greater).

Referring to FIGS. 1 and 3, in some embodiments, the two LED strings 55a, 55b are driven by the electronic driver 25 that can be positioned in the base of the two-in-one lamp 100. FIG. 3 is a block diagram illustrating the integration of light engine configuration, i.e., the light source 50, as depicted in FIG. 2, and the structure of the lamp 100, as depicted in FIG. 1, with a driver 25 and switch to a power source. The driver 25 can be configured to drive the two-in-one lamp 100 including the general illumination light mode and the substantially insect free illumination light mode. The driver 25 may drive the lamp 100 in (1) a first general illumination (GI) light mode wherein the first string of LEDs 55a is on at the desired correlated color temperature (CCT); and (2) a second emission mode which is the insect free illumination light mode wherein the second string of LEDs 55b is turned on. The change from the general illumination (GI) light mode to the substantially insect free illumination light mode, and vice versa, can be achieved with a very simple up and down flick, i.e., toggle, of the common household switch, e.g., rocker switch, such as a toggle wall switch used for room lighting in homes. In one example, to achieve this mode change, a commercial integrated circuit (IC), e.g., OZ2082C LED driver controller provided by $O_2$ Micro International Ltd can be used. The OZ2082C LED driver controller is one example of a driver 25 for use with the lamp 100, as depicted in FIGS. 1 and 3.

The operation of this driver 25 is described in greater detail below with reference to FIG. 3, wherein a light switch (switch 60) is communicatively coupled with the lamp base 15 (as depicted in FIG. 1) with which the lamp 100 is operatively coupled. In some embodiments, the lamp base 15 screws into the existing socket in the home. In some embodiments, the light switch 60 communicatively couples with the socket in the home. The operation is based on the hysteresis of the light switch. The switch is illustrated in FIG. 3 by reference number 60. By flicking the switch 60, i.e, changing the switch 60 from an on position to an off position, the lamp 100 will cycle through the general illumination light mode and the substantially insect free illumination light mode. The switch 60 may be, for example, a toggle light switch or rocker switch, configured as typically done, or any other suitable household or commercial type of lighting switch.

Referring to FIG. 3, the switch 60 may be in wired or wireless communication with the lamp 100. In some embodiments, when the lamp 100 is turned on initially by toggling the switch 60 to its on position, the lamp 100 will enter its first emission mode which is the general illumination light mode, which for example may be employed for lighting a porch. If the lamp 100 is then turned off (by toggling the switch 60 into its off position) and on again (by toggling the switch 60 to its on position) within a specified time window, the lamp 100 can enter the second emission mode, which is the substantially insect free illumination light mode. If the lamp 100 is thereafter turned off again (by toggling the switch 60 into its off position) and on again (by toggling the switch 60 to its on position) within a specified second time window, the lamp 100 will return to the first emission mode, which is the general illumination light mode.

The duration of each of the first and second time windows may be customized, as desired, and in at least some cases may be about 3 seconds or less. For example, in some embodiments, the duration of each of the first and second time windows may be about 2.5 seconds or less. In another example, the duration of each of the first and second time windows may be about 2 seconds or less. In yet another example, the duration of each of the first and second time windows may be about 1.5 seconds or less. In an even further example, the duration of each of the first and second time windows may be about 1 second or less. In some instances, either (or both) the first and second time windows may be user-programmable.

Referring to FIG. 3, in some embodiments, the driver 25 may be a single-channel or multi-channel electronic driver configured to drive the solid state light emitters, e.g., LEDs of the first and second strings of LEDs 55a, 55b, utilizing pulse-width modulation (PWM) dimming or any other suitable standard, custom, or proprietary driving techniques. As further shown in FIG. 3, the driver 25 may include a controller 26. In accordance with some embodiments, the driver 25 may be configured to provide a lamp 100 with a two-mode operation; that is, the driver 25 may provide lamp 100 with: (1) a general illumination light emissions mode in which the first string of LEDs 55a emit light having a CCT between 2700K and 6500K and a CRI greater than 80 and (2) a substantially insect free illumination light mode, in which the light wavelengths of the second string of LEDs 55b has wavelengths that are generally above 550 nm to be outside the wavelengths that are visible to insects, and hence provide an insect visible ratio of 5.8% or less.

In some embodiments, the lamp 100 having the general illumination lighting mode and the substantially insect free illumination light mode may be driven by the driver 25 including a controller 26 configured to support mode changing for the lamp 100 based, in part or in whole, on hysteresis. For example, mode changing of the lamp 100 may be based, in part or in whole, on the hysteresis phenomena of a switch 60, e.g., light switch, in operation toggling between ON and OFF electrical states. In accordance with some embodiments, the output of LEDs for the first and second string of LEDs 55a, 55b, and thus the lamp 100 may be electronically controlled by controller 26. To such ends, the controller 26 may be operatively coupled with the LEDs of the first and second string of LEDs 55a, 55b (or light source 50 more generally), for instance, by a communication bus or other suitable interconnect. In some embodiments, the controller 26 may be configured to communicate with the LEDs, i.e., solid state light emitters, via any one, or combination, of suitable standard, custom, or proprietary wired or wireless digital communications protocols, as will be apparent in light of this disclosure.

In some embodiments, the controller 26 may be configured to electronically control the individual strings of LEDs 55a, 55b, i.e., solid state light emitters, to provide lamp 100 with both general illumination light modes and substantially insect free illumination light modes. In some instances, color control may be provided by controlling the first and second strings of LEDs 55a, 55b, with only one string conducting at a time, thereby providing two-mode operation. To such ends, the controller 26 may host one or more lighting control modules, e.g., a general illumination light mode module 27 and a substantially insect free illumination light mode module 28, and may be programmed or otherwise configured to output one or more control signals that may be utilized in controlling the operation of a given solid state light emitter, e.g., string of solid state light emitters 55a, 55b of the lamp 100.

For example, in some embodiments, the general illumination light mode module 27 of the controller 26 may control the first string of LEDs 55a in emitting wavelengths having a correlated color temperature (CCT) between 2700K and 6500K. The general illumination light mode module 27 may contain instructions for operating the LEDs in the first string of LEDs 55a to provide, i.e., emit, any of the above described characteristics of light provided in the above description of the first string of LEDs 55a that refers to FIGS. 1 and 2. As illustrated in FIG. 3, the controller 26 of the driver 25 containing the general illumination light mode module 27 can be in electrical communication to the light source 50, and more specifically to the first string of LEDs 55a, through a communication bus providing for electrical communication between the driver and the light source 50 over which control signals may be transmitted.

For example, in some embodiments, substantially insect free light mode module 28 of the controller 26 may control the second string of LEDs 55b in emitting wavelengths that are not visible to insects, e.g., being greater than 550 nm. For example, the substantially insect free light mode module 28 of the controller 26 may control the second string of LEDs 55b to emit light having an insect visible ratio of 5.8% or less. The substantially insect free light mode module 28 may contain instructions, e.g., output signals to the second string of LEDs 55b, for operating the LEDs in the second string of LEDs 55b to provide, i.e., emit, any of the above described characteristics of light provided in the above description of the second string of LEDs 55b that refers to FIGS. 1 and 2. As illustrated in FIG. 3, the controller 26 of the driver 25 containing the substantially insect free light mode module 28 can be in electrical communication to the light source 50, and more specifically to the second string of LEDs 55b, through a communication bus providing for electrical communication between the driver and the light source 50 over which control signals may be transmitted.

In accordance with some embodiments, the general illumination light mode module 27 and the substantially insect free illumination light mode module 28 of the controller 26 may be implemented in any suitable standard, custom, or proprietary programming language, such as, for example, C, C++, objective C, JavaScript, or any other suitable instruction set, as will be apparent in light of this disclosure. The module(s) of controller 26 can be encoded, for example, on a machine-readable medium that, when executed by a processor, carries out the functionality of lamp 100, in part or in whole. The computer-readable medium may be, for example, a hard drive, a compact disk, a memory stick, a server, or any suitable non-transitory computer or computing device memory that includes executable instructions, or a plurality or combination of such memories. Some embodiments can be implemented, for instance, with gate-level logic, an application-specific integrated circuit (ASIC) or chip set, or other such purpose-built logic. Some embodiments can be implemented with a microcontroller having input/output capability (e.g., inputs for receiving user inputs; outputs for directing other components) and embedded routines for carrying out device functionality. In a more general sense, the functional modules of controller 26 can be implemented in any one, or combination, of hardware, software, and firmware, as desired for a given target application or end-use.

Moreover, in some embodiments, a given module of controller 26 (or controller 26 more generally) may be programmable to achieve any of the various functions and emissions capabilities desired of lamp 100 for a given target application or end-use. The present disclosure is not intended to be limited only to these example lighting control modules and output signals; as additional and/or different lighting control modules and output signals may be provisioned, as desired for a given target application or end-use.

Further, it is not intended to be limited only to drivers 25 including these specific example controllers 26. In a more general sense, and in accordance with some other embodiments, controller 26 can be any power supply controller IC or microcontroller having the ability to sense the operation of the input power (e.g., based on the on/off state of switch 60, discussed below) while maintaining a hysteresis from on-to-off and off-to-on control, with LED string control being provided by controlling the on/off state of the LEDs in the first and second string of LEDs 55a, 55b. In some still other cases, controller 26 may be a microcontroller programmed to receive a control input from a wired or wireless source other than, or in addition to, a switch (e.g., such as switch 60) and accordingly generate a target mode of lighting, e.g., a general illumination lighting mode or substantially insect free mode of lighting, by controlling the duty cycle of the first and second string of LEDs 55a, 55b.

Returning to FIG. 3, the lamp 100 optionally may include a communication module 70, which may be configured as a transmitter, a receiver, or both (i.e., a transceiver). In some cases, communication module 70 may be separate and distinct from controller 26 (e.g., as generally shown in FIG. 3), though in some other cases, communication module 70 may be a component of or otherwise integrated with controller 26. In accordance with some embodiments, controller 26 may be configured to output control signal(s) to the first and second strings of LEDs 55a, 55b based, at least in part, on input received from a remote source, such as a control interface 65. Control interface 65 may be physical, virtual, or a combination thereof and may be configured to communicate with the controller 26 (via intervening communication module 70), which in turn interprets input received from control interface 65 and distributes desired control signal(s) to the first and second strings of LEDs 55a, 55b of the light source 50. In some embodiments, the control interface 65 may be employed, in accordance with some embodiments, in changing the emissions modes of lamp 100. In some embodiments, the control interface 65 interacts with the switch 60, e.g., over the communications module 70, as the switch toggles from the ON and Off electrical states, and provides the signal to the driver 25. The driver 25 receiving the signal from the control interface employing the controller 26 sends a signal to illuminate either the first string of LEDs 55a to provide a general illumination light mode, or the second string of LEDs 55b to provide a substantially insect free illumination light mode.

To such ends, the communication module 70 and control interface 65 may be configured for wired or wireless communication (or both) utilizing any one, or combination, of suitable means, such as Universal Serial Bus (USB), Ethernet, FireWire, Wi-Fi, Bluetooth, or ZigBee, among others.

Optionally, the control interface 65 may be or otherwise employ a touch-sensitive display or surface, such as a touchpad or other device with a touch-based user interface (UI) or graphical UI (GUI), as provided by a computing device, mobile or otherwise. Other suitable configurations for the communication module 70 and the control interface 65 will depend on a given application.

Referring to FIGS. 1-3, the lamp 100 including the electronics, e.g., the driver 25 including the controller 26 and the light source 50, is operatively coupled with the lamp base 15, which can provide for electrical communication between the lamp 100 and a lamp fixture. In some embodiments, the lamp base 15 screws into the existing socket in the home. In some embodiments, the light switch 60 communicatively couples with the socket in the home. As can be seen from these figures, the lamp 100 may include a body portion 10, the material, geometry, and dimensions of which may be customized, as desired for a given target application or end-use. The body portion 10 of the lamp 100 is configured to house the lamp electronics, e.g., driver 25 and light source 50, and is operatively coupled with a given lamp base 15 which screws into the existing home socket so that power may be delivered to lamp 100 for operation thereof. To that end, lamp base 15 may be of any standard, custom, or proprietary contact type and fitting size, as desired for a given target application or end-use. In some cases, such as those illustrated in FIGS. 1-3, the lamp base 15 may be configured as a threaded lamp base including an electrical foot contact (e.g., an Edison-type screw base of size E26 or E27). In some other cases, the lamp base 15 can be configured, for example, as a bi-pin, tri-pin, or other multi-pin lamp base, a twist-lock mount lamp base, or a bayonet connector lamp base, to name a few. Other suitable configurations for the body portion 10 (also referred to as a lamp housing) and the lamp base 15 can depend on a given application.

Referring to FIG. 1, the lamp 100 can optionally include a heatsink portion 45 configured to be in thermal communication with light source 50 to facilitate heat dissipation for the lamp 100. To that end, optional heatsink portion 45 may be of monolithic or polylithic construction and formed, in part or in whole, from any suitable thermally conductive material. For instance, optional heatsink portion 45 may be formed from any one, or combination, of aluminum (Al), copper (Cu), gold (Au), brass, steel, or a composite or polymer (e.g., ceramics, plastics, and so forth) doped with thermally conductive material(s). The geometry and dimensions of optional heatsink portion 45 may be customized, as desired for a given target application or end-use. In some instances, a thermal interfacing layer (e.g., a thermally conductive tape or other medium) optionally may be disposed between heatsink portion 45 and light source 50 to facilitate thermal communication there between. Other suitable configurations for optional heatsink portion 45 and optional thermal interfacing layer will depend on a given application.

As will be appreciated in light of this disclosure, the lamp 100 may further include or otherwise have access to any of a wide range of other electronic components employable with solid-state lamps, e.g., light emitting diodes (LEDs) and luminaires. For instance, in some embodiments, the lamp 100 may include or otherwise have access to power conversion componentry, such as electrical ballast circuitry, configured to convert an AC signal into a DC signal at a desired current/voltage to power a given light source 50. In some instances, the lamp 100 may include self-ballasted electronics (e.g., disposed within base portion 10 or other portion of lamp 100). In some embodiments, the lamp 100 may include or otherwise have access to processing componentry, such as a central processing unit (CPU) or a microcontroller unit (MCU), among others.

Returning to FIG. 1, the lamp 100 may also include one or more optics 20, e.g., lens, which may have any of a wide range of configurations. A given optic 20 may be configured to transmit, in part or in whole, emissions received from a given string of the first and second strings of LEDs 55a, 55b of the light source 50 that is positioned behind the given optic 20 and housed within the base portion 10 of the lamp 100. The optic 20 may be formed from any one, or combination, of suitable optical materials. For instance, in some embodiments, the optic 20 may be formed from a polymer, such as poly(methyl methacrylate) (PMMA) or polycarbonate, among others. In some embodiments, the optic 20 may be formed from a ceramic, such as sapphire ($Al_2O_3$) or yttrium aluminum garnet (YAG), among others. In some embodiments, the optic 20 may be formed from a glass. In some embodiments, the optic 20 can be formed from a combination of any of the aforementioned materials. Furthermore, the dimensions and geometry of the optic 20 may be customized, as desired for a given target application or end-use. In some embodiments, the optic 20 may be or otherwise include a lens, such as a Fresnel lens, a converging lens, a compound lens, or a micro-lens array, to name a few. In some embodiments, the optic 20 may be or otherwise include an optical dome or optical window. In some cases, the optic 20 may be formed as a singular piece of optical material, providing a monolithic optical structure. In some other cases, the optic 20 may be formed from multiple pieces of optical material, providing a polylithic (multi-piece) optical structure. In some instances, the optic 20 may be configured to filter light transmitted therethrough. Other suitable configurations for optic(s) 20 will depend on a given application and will be apparent in light of this disclosure.

In some embodiments, the lamp 100 that is described herein is unique to other lamps in the market because the lamp 100 described herein can provide two illumination light modes in a single lamp structure, i.e., a two-in-one design, in which one of the lighting modes is for general illumination and the other light mode provides a bug lamp, i.e., provides an insect free illumination light mode. Further, the lamp 100 that is described herein has the ability to switch between the general illumination operation, i.e., the general illumination light mode, and bug lamp operation, i.e., the substantially insect free illumination light mode, by the simple operation of a household switch. In some embodiments, the lamp 100 can provide superior bug mode spectrum compared to other bug lamps in the market. More specifically, in some embodiments, the lamp 100 of the present disclosure emits light when in the substantially insect free illumination light mode having a lower visible bug ratio than conventional bug lamps.

Although the lamp 100 having the general illumination light mode and the substantially insect free illumination light mode has been described generally above, the following examples are provided to further illustrate the lamp structures and methods described herein and to demonstrate some advantages that arise therefrom. It is not intended that the present disclosure be limited to the specific examples described hereafter.

EXAMPLES

Figure 4:
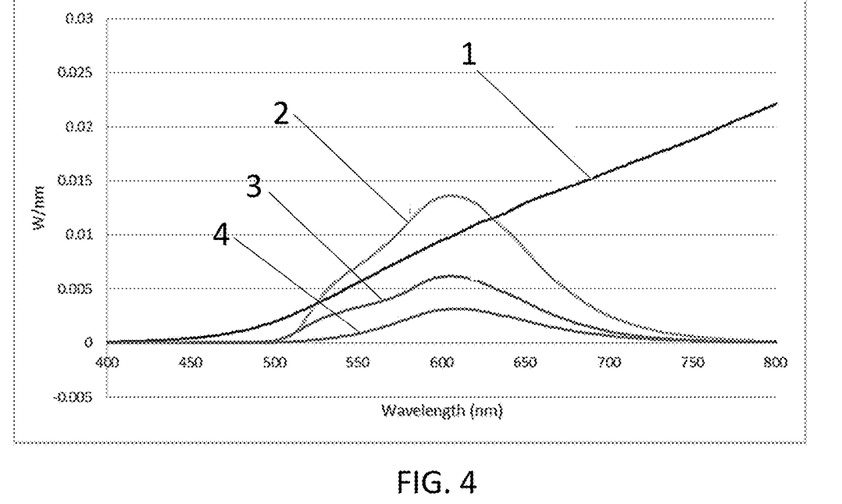
FIG. 4 is a plot depicting the spectral power distribution (SPD) of four bug lamps for comparative examples illustrating the range of wavelengths they emit.

FIG. 4 is a plot depicting the spectral power distribution (SPD) of four lamps for comparative examples illustrating the range of wavelengths they emit. FIG. 4 illustrates the spectrum intensity as a function of the wavelength for these four comparative sample lamps. The comparative sample lamps having the SPD plotted in FIG. 4 are considered typical for conventional marketplace available bug lamps.

The comparative sample lamp that provided the spectral power distribution (SPD) identified by reference number 1 is an incandescent bug lamp. The W/nm of lamp that provided the plot identified by reference number 1 in FIG. 4 increases monotonically with wavelength. This lighting characteristic is typical of incandescent technology. In incandescent bug lamps, an inorganic yellow powder is used as a coating on the interior of the glass bulb. As a result, the lamp that provided the spectral power distribution (SPD) identified by reference number 1 appears yellow when not illuminated.

The comparative sample lamps that provided the spectral power distribution (SPD) plots identified by reference numbers 2, 3 and 4 were bug lamps that employ LED light sources. Unlike the comparative sample lamp that employed the incandescent light source, the comparative sample lamps that employed the LED light sources exhibited a local maximum in the spectral power distribution (SPD) between 606 nm and 610 nm due to the light waves emitted by the LEDs used in these comparative lamps. For the lamps that provided the plots identified by reference numbers 2 and 3, the light source of the comparative lamps was a white LED, in which the light source further included a yellow coating on the inside of the bulbs. The lamps that provided the plots identified by reference numbers 2 and 3 appeared yellow when not illuminated. The lamp that provided the plot identified by reference number 4 employed an LED light source, but did not employ a yellow coating on the bulb. The lamp that provided the plot identified by reference number 4 appeared white when not illuminated, but when illuminated, the bulb lighted up with a yellow color.

Table I includes the calculated "insect visible ratio" from the spectral power distributions (SPDs) measured from the four comparative sample lamps plotted in FIG. 4.

TABLE I

| % Power <550 nm/<700 nm: Insect Visible Ratio | | | |
|---|---|---|---|
| COMP LAMP 1 | COMP LAMP 2 | COMP LAMP 3 | COMP LAMP 4 |
| 13.20% | 11.90% | 13.95% | 5.95% |

The insect visible ratio (or the visible insect ratio) is the spectral power <550 nm (which is substantially visible to most insects) divided by the spectral power in the whole visible spectrum (400 nm-700 nm), expressed as a percentage. The comparative sample lamp identified by reference number 3 in FIG. 4 (identified as COMP LAMP 3 in Table 1) has an insect visible ratio of 13.9%, which is followed by the comparative sample lamp identified by reference number 1 in FIG. 4 (identified as COMP LAMP 1 in Table 1) that had an insect visible ratio of 13.2%. Further, the comparative sample lamp identified by reference number 2 in FIG. 4 (identified as COMP LAMP 2 in Table 1) had an insect visible ratio of 11.9%. The comparative sample lamp identified by reference number 4 (identified as COMP LAMP 4) had the lowest insect visible ratio of the comparative lamp samples with an insect visible ratio of 5.95%.

Figure 5:
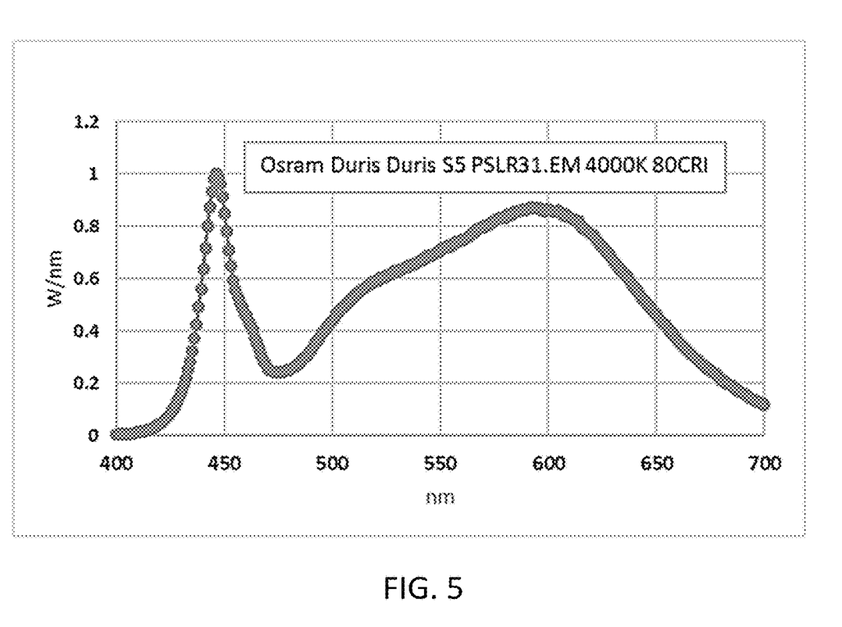
FIG. 5 is a plot depicting the single spectral power distribution of light emitted from a light emitting diode (LED) used in a first string of LEDs that provide a general illumination light mode in the light source of a test lamp sample including two modes of illumination, i.e., a general illumination light mode and an insect free illumination light mode.

Test lamp samples were provided including two modes of lighting in a two in one configuration consistent with the lamps described in the present disclosure with reference to FIGS. 1-3. The first mode of lighting for the test lamp samples was a general illumination light mode, and the second mode of lighting for the test lamp was an insect free illumination light mode. The two modes of lighting were provided by a light source including two strings of LEDs 55a, 55b, as described above with reference to FIG. 2. The general illumination light mode was provided by a first string of LEDs 55a with a correlated color temperature (CCT) between 2700K and 6500K. For each of the test lamp samples, the first string of LEDs 55a employed 8 Osram Duris S5 GW PSLR31.EM 4000K 80 CRI LEDs. FIG. 5 is a plot depicting the single spectral power distribution of light emitted from aforementioned example of a light emitting diode (LED) used in a first string of LEDs that provided the general illumination light mode in the light source of the test lamp samples.

Figure 7:
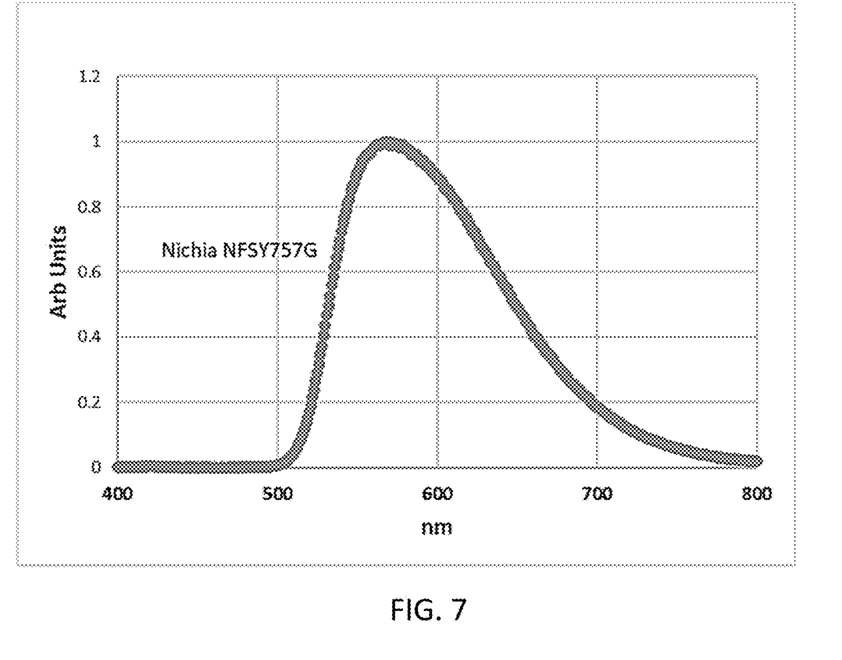
Figure 8:
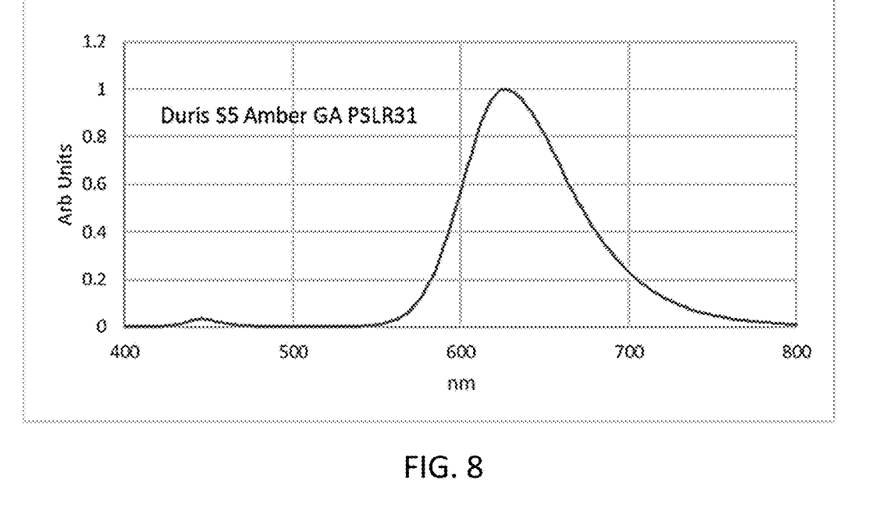

The substantially insect free illumination light mode of the test lamp samples was provided by a second string of LEDs 55b with insect visible ratio that was no greater than 5.8%. Consistent with the lamp 100 described above with reference to FIGS. 1-3, the second string of LEDs 55b for the test lamp samples was designed provide an emission spectrum that is efficacious for bug lamp operation by minimizing the ratio of the spectral power <550 nm relative to the overall visible power. This ratio is the "insect visible ratio". Three test lamp samples, LE1, LE2, LE3, were provided having different arrangements of light emitting diodes in the second string of LEDs 55b, while the first string of LEDs 55a for each of the three test lamp samples was the same. In a first test lamp sample (LE1), the second string of LEDs 55b includes six (6) Osram Duris S5 Amber GA PSLR31 LEDs and three (3) Nichia NFSY757G LEDs in series. In a second test lamp sample (LE2), the second string of LEDs 55b includes six (6) Osram Duris S5 Amber GA PSLR31 LEDs and three (3) Osram Duris S5 GW PSLR31.CM 2000K 90 CRI LEDs. In a third test lamp sample (LE3), the second string of LEDs 55b includes nine (9) Osram Duris S5 Amber GA PSLR31 LEDs. FIGS. 6-8 are plots depicting the single spectral power distribution of light emitted from aforementioned examples light emitting diodes (LEDs) used in a second string of LEDs that provided the insect free illumination light mode in the light source of the test lamp samples.

Figure 9:
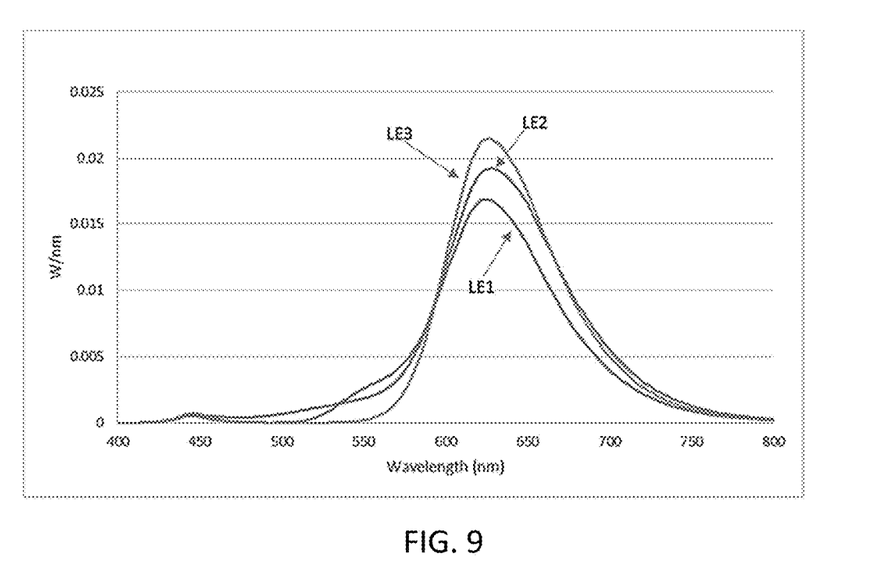
FIG. 9 is a plot depicting shows the spectral power distribution (SPD) of light emitted by the substantially free of insect mode of lighting for three test lamp structures, in accordance with some embodiments of the present disclosure.

FIG. 9 is a plot depicting the spectral power distribution (SPD) of light emitted by the substantially insect free illumination light mode for the three test lamp structures. The SPD is shown for the three test samples identified above as LE1, LE2 and LE3. Table II shows the calculated "insect visible ratio" from the SPDs of the test sample lamps plotted in FIG. 9 having a light source including an insect free illumination light mode consistent with the lamps 100 described above with reference to FIGS. 1-3 of the disclosure.

TABLE II

| % Power <550 nm/<700 nm | | |
|---|---|---|
| LE1 | LE2 | LE3 |
| 4.30% | 5.70% | 1.40% |

The test sample lamp designated as LE2 had an insect visible ratio of 5.7%, followed by the test sample lamp designated as LE1, which had an insect visible ratio of 4.3%. The test sample lamp designated as LE3 had an insect visible ratio of 1.4%. Comparison of the insect visible ratio data recorded in Table II with the insect visible ratio data recorded in Table I illustrates that all the three test sample lamps, i.e., LE1, LE2, LE3, which each had a second string of LEDs consistent with the lamp 100 described in the present disclosure with reference to FIGS. 1-3, had lower insect visible ratios than the comparative sample lamps described with reference to FIG. 4 and Table I. The comparative sample lamps are considered typical for conventional marketplace available bug lamps. For example, review of the insect visible ratios for the test sample lamps designated as LE1 and LE2 and LE3 with the insect visible ratios of the comparative sample lamps recorded in Table I illustrates distinctly lower insect visible ratio provided by the lamps of the present disclosure, e.g., the lamp 100 described with reference to FIGS. 1-3, to the conventional bug lamps available in the marketplace.

Figure 10:
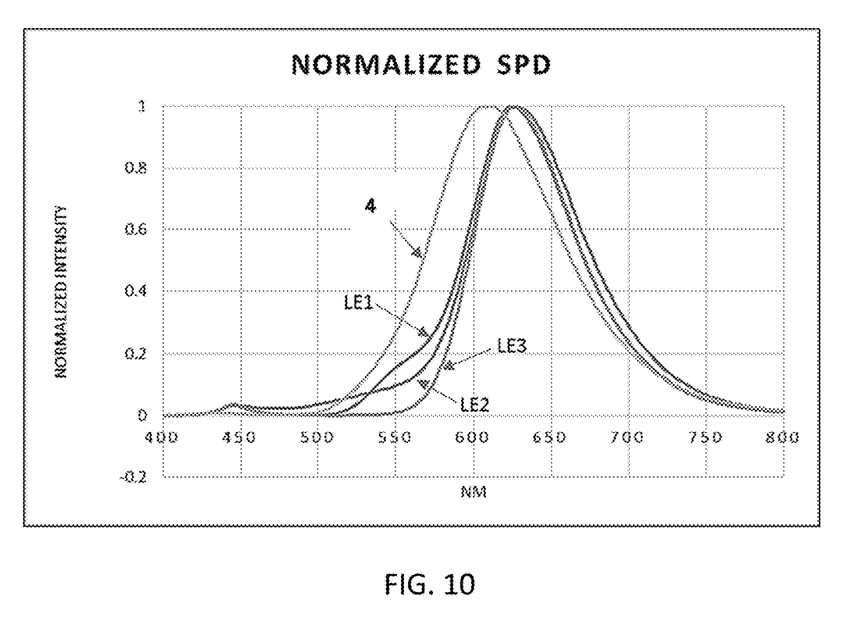
FIG. 10 is a plot depicting the normalized spectral power distribution (SPD) for the embodiments of the lamp that were plotted in FIG. 9 in combination with the spectral power distribution (SPD) being plotted for one example of a comparative example lamp that is plotted in FIG. 4.

FIG. 10 is a plot depicting the normalized spectral power distribution (SPD) for the test sample lamps, i.e., LE1, LE2, LE3 that were plotted in FIG. 9, in combination with the spectral power distribution (SPD) being plotted for one example of a comparative sample lamp that was plotted in FIG. 4. The comparative sample lamp identified by reference number 4 in FIG. 4 was plotted as an overlay in FIG. 10, because it was the lowest insect visible ratio of the lamps included in the comparative sample lamps. The lowest insect visible ratio of the lamps included in the comparative sample lamps is equivalent to the best case scenario for a marketplace bug lamp. The SPD in FIG. 10 are obtained from the relevant SPDs in FIG. 9 and FIG. 4 by dividing the local intensity at each wavelength by the maximum local intensity of each relevant SPD. As illustrated by the plot depicted in FIG. 10, the difference between wavelengths emitted by the test sample lamps (provided by the plots for LE1, LE2, LE3) and the comparative sample lamps (provided by the plot having reference number 4), which is indicative of a marketplace bug lamp, is evident not only in the maximum peak wavelength, but also in the shape of the curves below 550 nm and also in the full width half maximum (FWHM).

Table III compares the peak wavelength of the test sample lamps having SPD plotted in FIG. 9 vs. the comparative sample lamp having the SPD identified by reference number 4 that is plotted in FIG. 4.

TABLE III

| | Max Wavelength | |
|---|---|---|
| Lamp | Max λ Power, nm | FWHM, nm |
| LE1 | 624 | 79.5 |
| LE2 | 628 | 83 |
| LE3 | 626 | 75 |
| COMP LAMP 4 | 610 | 95 |

It is noted that the peak wavelength of the comparative sample lamp having the plot identified by reference number 4 in FIGS. 4 and 10 is 610 nm, whereas the peak wavelength of the test sample lamps, i.e., LE1, LE2, LE3, which had a second string of LEDs 55b consistent with the lamp 100 described in the present disclosure with reference to FIGS. 1-3, is higher and is between 624 nm and 628 nm. The full width half maximum (FWHM) denotes the difference in nm between the upper and lower wavelengths at which the normalized SPD intensity is 50%. It is noted from Table III that the full width half maximum (FWHM) for the test sample lamps, i.e., LE1, LE2, LE3, is distinctly different from and lower than the representative comparative sample lamp included in Table III. For example, the test sample lamps, i.e., LE1, LE2, LE3, had FWHM values that were recorded in Table III that ranged from 75 nm to 83 nm. In comparison, the comparative sample layer having the plot identified by reference number 4 in FIGS. 4 and 10, which is indicative of a conventional marketplace bug lamp, had a FWHM value of 95 nm, as recorded in Table III.

The insect visible ratio measured from the test sample lamps LE1, LE2, LE3, which are indicative of performance of some embodiments of lamps 100 that have been described with reference to FIGS. 1-3, is also distinctly lower than that for the comparative test sample. More specifically, the test sample lamps designated LE1 and LE3 had insect visible ratios of 4.3% and 1.4%, while the comparative sample lamp that provided the plots identified by reference number 4 in FIGS. 4 and 10 had an insect visible ratio of 5.95%. This comparative sample lamp had lighting performance equivalent to the best lighting performance for bug lamp applications possible with commercially available bug lamps. Although not intending to be bound, for the purposes of completeness, in some instances the aforementioned difference in the insect visible ratio was primarily due to the difference in the shape of the curves in FIG. 10 below 550 nm for the comparative sample lamp having the plot identified by reference number 4 vs the test sample lamps LE1, LE2 LE3.

The above embodiments and examples are given above to illustrate the scope and spirit of the present invention. These embodiments and examples will make apparent, to those of ordinary skill in the art, other embodiments and examples. These other embodiments and examples are within the contemplation of the present invention. Therefore, the present invention should be limited only by the appended claims.

What is claimed is:

1. A lamp assembly comprising:
 a housing including a body for containing light sources, the body having a first end for engagement to an electrical source for energizing the light sources contained within the body, and the body includes a second end having a lens through which the light sources emit light;
 a first group of solid state light emitters providing one grouping of said light sources contained within the housing, wherein illuminated the first group of solid state light emitters produces a general illumination light mode provided by a first range of light wavelengths emitted by the first group of solid state light emitters;
 a second group of solid state light emitters providing another grouping of said light sources contained within the housing, wherein illuminated the second group of said light sources contained within the housing produces a substantially insect free illumination light mode that emits a second range of light wavelengths that are not visible to insects, the second range of wavelengths having a substantial majority being greater than 550 nm; and
 a driver to illuminate only one of the first and second groups of solid state light emitters at a time so that the first and second rounds of solid state light emitters cannot emit light simultaneously, wherein switching between the first and second group of solid state light emitters is provided by a controller in the driver for energizing one of the first and second group of solid state light emitters, the controller being based upon hysteresis of a rocker lighting switch that provides an external switch to the lamp assembly.

2. The lamp assembly of claim 1, wherein the second range of light wavelengths has a spectral power ratio of wavelengths of less than substantially 550 nm to a total spectra of less than 700 nm, that is equal to 5.8% or less.

3. The lamp assembly of claim 1, wherein the solid state light emitters for the first and second group of said solid state light emitters are selected from the group consisting of semiconductor light-emitting diodes (LEDs), organic light-emitting diodes (OLED), polymer light-emitting diodes (PLED) and combinations thereof.

4. The lamp assembly of claim 1, wherein the first range of light wavelengths emitted by the first group of solid state light emitters has a correlated color temperature (CCT) ranging from 2700K to 6500K.

5. The lamp assembly of claim 1, wherein the second range of light wavelengths emitted by the second group of solid state light emitters have a correlated color temperature (CCT) ranging from 1000 K to 1400 K.

6. The lamp assembly of claim 1, wherein the first range of light wavelengths emitted by the first group of solid state light emitters have a color rending index (CRI) ranging from 70 to 95.

7. The lamp assembly of claim 1, wherein the second range of light wavelengths emitted by the second group of solid state light emitters have a distribution with peak wavelength between 620 nm to 630 nm.

8. The lamp assembly of claim 1, wherein the second range of light wavelengths emitted by the second group of solid state light emitters emits said second range of light wavelengths having a full width half maximum between 70 nm and 85 nm.

9. The lamp assembly of claim 1, wherein the controller providing said switching based upon hysteresis of said rocker lighting switch comprises a first rocker setting providing an off position, and a second rocker setting providing an on position, wherein in turning the lamp assembly on by a first toggling of the rocker lighting switch from the off position to the on position illuminates said first group of solid state light emitters providing said general illumination light mode, and wherein a second toggling of the rocker lighting switch from the on position to the off position de-illuminates the first group of solid state light emitters, and illuminates said second group of solid state light emitters providing said substantially insect free illumination mode.

10. The lamp assembly comprising:
a housing including a body for containing light sources, the body having a first end for engagement to an electrical source for energizing the light sources contained within the body, and the body includes a second end having a lens through which the light sources emit light;
a first group of solid state light emitters providing one grouping of said light sources contained within the housing, wherein illuminated the first group of solid state light emitters produces a general illumination light mode, in which the general illumination light mode is provided by a first range of light wavelengths emitted by the first group of solid state light emitters having a correlated color temperature ranging from 2700K to 6500K; and
a second group of solid state light emitters providing another grouping of said light sources contained within the housing, wherein illuminated the second group of said light sources contained within the housing emit a second range of light wavelengths that are not visible to insects for a substantially insect free illumination light mode, the second range of light wavelengths having a spectral power ratio of wavelengths of less than substantially 550 nm to a total spectra of less than 700 nm, that is equal to 5.8% or less, wherein switching between the first and second group of solid state light emitters is provided by a controller for energizing one of the first and second group of solid state light emitters, the controller being based upon hysteresis of a rocker lighting switch that provides an external switch to the lamp assembly.

11. The lamp assembly of claim 10, wherein the second group of solid state light emitters includes at least two LED types each LED type emitting a different spectra of wavelengths of lights.

12. The lamp assembly of claim 10, wherein the second range of light wavelengths have a spectral power ratio of wavelengths of less than substantially 550 nm to a total spectra of less than 700 nm, that is equal to 4.5% or less.

13. The lamp assembly of claim 10, wherein the second range of light wavelengths have a spectral power ratio of wavelengths of less than substantially 550 nm to a total spectra of less than 700 nm, that is equal to 1.5% or less.

14. The lamp assembly of claim 13, wherein the second group of solid state light emitters includes a string of light emitting diodes comprising a single LED type that emits a single spectra of wavelengths of light.

15. An illumination method comprising:
energizing one grouping of solid state light sources in a lamp having a plurality of solid state light sources behind a lens within a single lamp housing; and
switching from a first grouping of solid state light sources for a general lighting mode of the lamp that emits first light wavelengths that include light that is visible to insects to a second grouping of solid state light sources emitting second light wavelengths that in their majority are not visible to insects, the second light wavelengths having a spectral power ratio of wavelengths of less than substantially 550 nm to a total spectra of less than 700 nm, that is equal to 5.8% or less, wherein said switching is responsive to a switch that is external from the single lamp housing, wherein said switching is provided by a controller in a driver for said energizing one grouping of the solid state light sources, the controller being based upon hysteresis of a rocker lighting switch providing said external switch.

16. The illumination method of claim 15, wherein the controller providing said switching based upon hysteresis of said rocker lighting switch comprises a first rocker setting providing an off position, and a second rocker setting providing an on position, wherein in turning the lamp assembly on by a first toggling of the rocker lighting switch from the off position to the on position illuminates said first group of solid state light emitters providing said general illumination light mode, and wherein a second toggling of the rocker lighting switch from the on position to the off position de-illuminates the first group of solid state light emitters, and illuminates said second group of solid state light emitters providing said substantially insect free illumination mode.

17. The illumination method of claim 15, wherein the second light wavelengths have a spectral power ratio of wavelengths of less than substantially 550 nm to a total spectra of less than 700 nm, that is equal to 1.5% or less.

* * * * *